United States Patent [19]
Holland

[11] Patent Number: 5,735,835
[45] Date of Patent: Apr. 7, 1998

[54] FEMALE EXTERNAL URINARY COLLECTION POUCH

[76] Inventor: Marlan J. Holland, 8775 San Gregorio, Atascadero, Calif. 93422

[21] Appl. No.: 736,535

[22] Filed: Oct. 24, 1996

[51] Int. Cl.⁶ .......................................... A61F 5/44
[52] U.S. Cl. .................. 604/331; 604/327; 604/329; 604/352
[58] Field of Search ............... 604/323, 327–331, 604/349, 353, 352, 179, 180; 602/79

[56] References Cited

U.S. PATENT DOCUMENTS

| | | | |
|---|---|---|---|
| 3,194,238 | 7/1965 | Breece | 128/295 |
| 3,995,329 | 12/1976 | Williams | 4/110 |
| 4,198,979 | 4/1980 | Cooney et al. | 128/295 |
| 4,246,901 | 1/1981 | Michaud | 604/329 |
| 4,350,785 | 9/1982 | Habib | 524/55 |
| 4,421,511 | 12/1983 | Steer et al. | 604/329 |
| 4,484,917 | 11/1984 | Blackmon | 604/327 |
| 4,496,355 | 1/1985 | Hall et al. | 604/327 |
| 4,568,339 | 2/1986 | Steer | 604/329 |
| 4,681,572 | 7/1987 | Tokarz et al. | 604/329 |
| 4,690,677 | 9/1987 | Erb | 604/329 |
| 4,795,449 | 1/1989 | Schneider et al. | 604/329 |
| 4,846,819 | 7/1989 | Welch | 604/329 |
| 4,889,532 | 12/1989 | Metz et al. | 604/330 |
| 4,889,533 | 12/1989 | Beecher | 604/330 |
| 4,904,248 | 2/1990 | Vaillancourt | 604/329 |
| 5,053,027 | 10/1991 | Manfredi | 604/327 |
| 5,263,947 | 11/1993 | Kay | 604/331 |

OTHER PUBLICATIONS

Female Urinary Pouch 9840, "*Instructions for using the Hollister® Female Urinary Incontinence Pouch,*" 1986.

*Primary Examiner*—Robert A. Clarke
*Attorney, Agent, or Firm*—Merchant, Gould, Smith, Edell, Welter & Schmidt

[57] ABSTRACT

A female urinary collection device includes a receptacle pouch for collecting urine. The receptacle pouch includes a first area for securing two strips of tape, one to each buttock of a user to create a relatively rigid engagement of the device with the body. In the upper zone, there is a stretch loop and foam belt for securing the pouch around the waist. Inside the receptacle pouch, there is a reservoir of adsorbent material with a wick which exits the receptacle pouch through a tubing connected to an orifice in the receptacle. The receptacle pouch fits around the labia majora of the user.

20 Claims, 2 Drawing Sheets

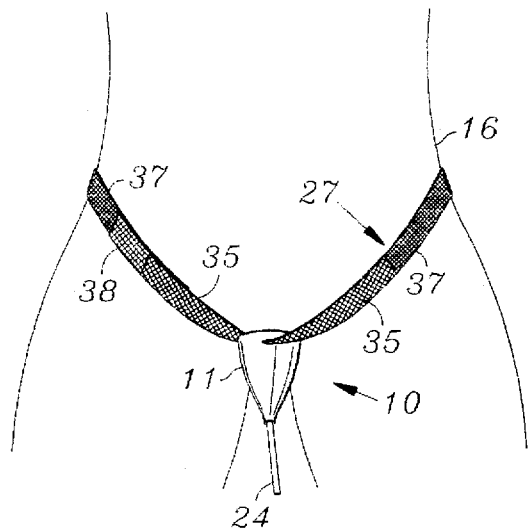
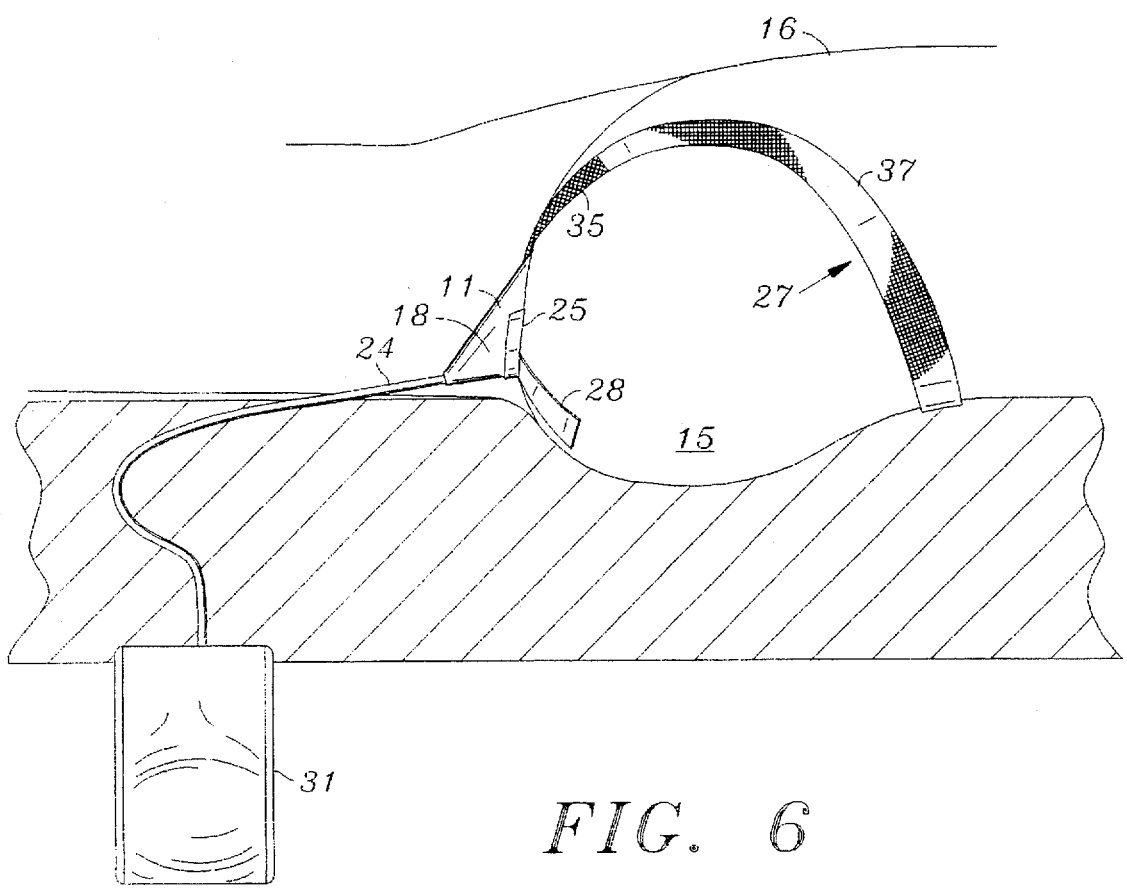

FEMALE EXTERNAL URINARY COLLECTION POUCH

BACKGROUND

Urinary incontinence is a common medical problem. Providing an effective system for collecting urine from incontinent human females is valuable.

Many systems have been devised for attempting to collect urine from human females afflicted with incontinence. These systems include the use of catheters, incontinence pads, and diapers.

The use of invasive catheters through the urethra into the bladder is relatively uncomfortable and can be dangerous to health due to the high incidence of urinary tract infection. Absorbent products which hold urine in contact with the skin for extended periods of time contribute to skin breakdown, sometimes resulting in serious decubitus ulcers. On the other hand, the efforts to locate devices in and around the anatomy of the female tissues constituting the external organs of generation is difficult since it is particularly problematic to obtain a relatively leak proof fit. The anatomy of each user is different and hence it is difficult to find a universally acceptable external urinary collection device for neatly mating with the human body in an effective leak proof manner in which urine can be removed from the body after voiding.

The present invention is directed to minimizing the disadvantages of currently-known urinary collection devices for human females. The invention provides a collection device which is comfortable to wear, minimizes leakage of urine, and is adaptable to accommodate many shapes of different female anatomies.

SUMMARY

According to the invention, a female urinary collection device includes a generally pouch-shaped receptacle for collecting urine from the urethra orifice of a female user.

The receptacle includes a bottom edge portion and a side wall portion projecting upwardly therefrom. There is a lip portion having a portion of foam tape attached along the edge for providing a generally compliant area for engagement around the external labia majora of the user. The portion adjacent to the bottom edge includes two tapes which act as a primary securing means to secure the receptacle firmly to the buttocks of the user. Adhesive affects the fixation.

A second securing means located at the top of the side wall adjacent to an upper edge provides for the use of a stretch loop and foam material to extend around the waist and permit securing the receptacle in a relatively flexible manner with the body of the user. The top portion of the receptacle above the lip is relatively open to permit spreading around the body portion and to permit for an accommodating fit with the user.

Within the receptacle there is contained a cone-shaped reservoir which has a wicking system which drains through an orifice into a tubing. The tubing is located in the orifice between a base edge and a bottom edge of the receptacle.

The tubing is directed to a collection bag intended to be located below the receptacle. The wick feeds urine under gravity from the reservoir into the tube and down into the collection bag.

The invention is further described with reference to the accompanying drawings.

DRAWINGS

FIG. 5 is a top view of the device worn by a user.

FIG. 6 is a side view of the device worn by a user lying horizontal on a mattress.

DESCRIPTION

Figure 1:
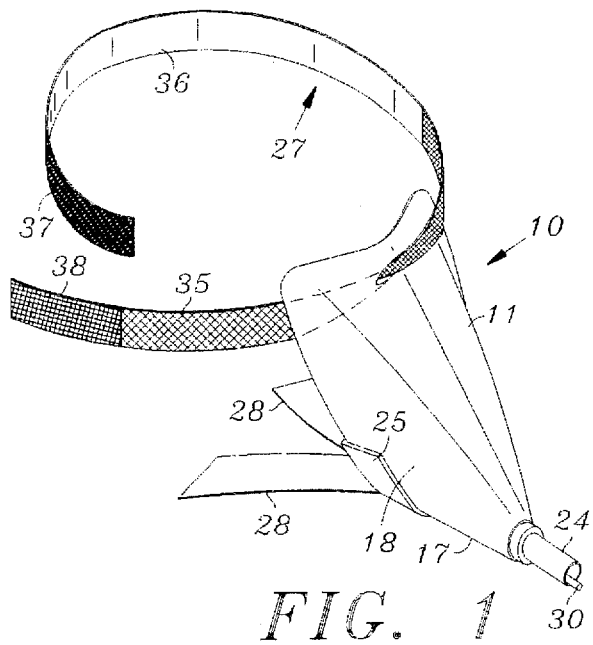
FIG. 1 is a perspective view of the device.

A female urinary collection device 10 comprises a generally pouch-shaped receptacle 11 for collecting urine from the urethral orifice of a female user 12.

The external organs of generation 13 in the human female are the mons Veneris, the labia majora 14, the menora, the clitoris, the meatus urinarius, and the orifice of the vagina. The meatus urinarius is also referred to as the orifice of the urethra. Below and rearwardly are the two buttock regions 15 of the human anatomy. Above the external organs and the buttock regions 15 is the waist portion 16 of the human form.

The receptacle pouch 11 has a bottom edge portion 17 and a side wall portion 18 projecting generally upwardly from the bottom edge portion 17. The side wall 18 and bottom edge 17 end in a lip portion 19 for sealing engagement with the area around the labia majora 14 of the user.

The side wall portion 18 is sized to extend from below the lips of the labia majora 14 to a position above those lips.

Figure 2:
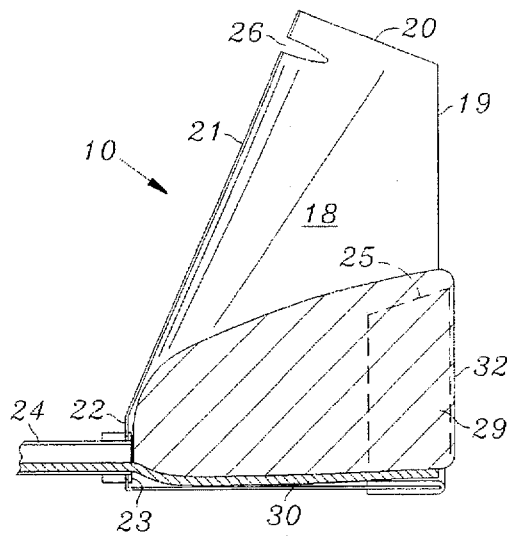
FIG. 2 is a side view of the device.
Figure 3:
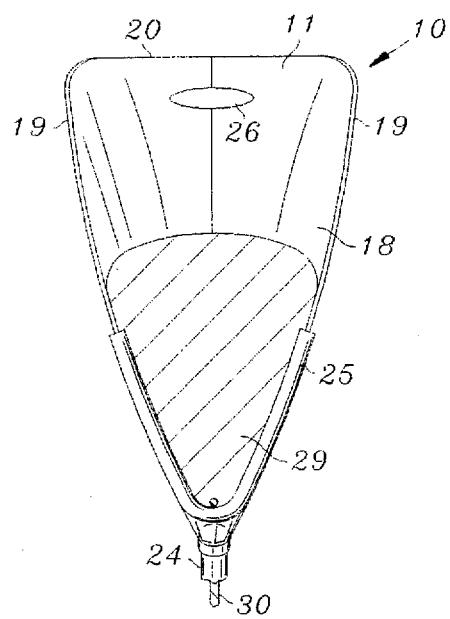
FIG. 3 is a front view of the device.
Figure 4:
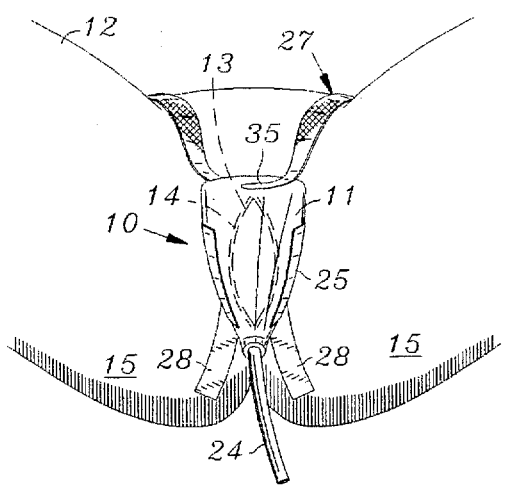
FIG. 4 is an end view of the device worn by a user.

Generally, the receptacle pouch 11 as formed by the side wall, when viewed from the side (FIG. 2) and in collapsed or closed unused form, adopts a relatively trapezoidal profiled shape of two half mating side walls 18. There is the bottom edge 17, the lip portion 19, an upper edge portion 20, and a base edge portion 21. Between the intersection of the base edge and bottom edge portions, there is an edge section 22 for accommodating an orifice 22 through which a drain tube 24 passes. This intersecting edge 22 is a portion which is rectangularly formed relative to the bottom edge 17. In this sense, the generally trapezoidal sectional view has an additional small intersecting edge portion 22 thereby creating a pentagonal shape.

When viewed from the front in an opened operative position the two half side portions 18 form a contiguous sheet and is shaped to have a substantially horizontal upper edge 20. From the ends of the upper edge 20 there are two depending substantially vertical lip portions 19. About half way down their length these vertical sections start to converge ultimately to a point adjacent the bottom edge 17.

The shape of the receptacle pouch when viewed from the front, namely the direction normally adhering to the human form, can be considered to be substantially curved edge triangulated form with rounded corners between the straight upper edge 20 and between the curved lips 19 and bottom edge 17. A generally curved V-shaped structure forms part of the wall of that triangulated shape.

The lip edge 19 includes a polyethylene closed cell foam tape 25 attached along the edge 19 to provide a soft surface to add comfort and reduce leakage of urine from the urethra and past the walls of the receptacle 11. The tape 25 is formed to cover the edge of the lip 19 both inside and outside of the receptacle pouch 11. As such, the tape 25 extends along the side wall 18 both on the inside of each side wall 18 half portion 18 and the outside of each side wall half portion 18. The length of the tape 25 extends at least about two inches up the lip portion 19 of the receptacle pouch 11. When viewed from the front, the tape 25 forms a substantially V-shaped trough portion extending up one side wall half portion 18 through the bottom edge portion 17 and up the opposite side wall half portion 18.

Cut into the base edge 21 of the receptacle pouch 11, which is formed of a vinyl sheet, there is formed an oval slot 26 to accommodate a belt 27 of about 1.5 inches width. The upper edges of the vinyl sheet of each half wall portion 18 can be separated so that it can spread apart and thus conform to different shapes of the human form. The belt 27 is preferably made of nylon stretch loop portion 35 and non-stretchable velfoam portion 36 which will extend up around the waist 16 and return to the receptacle 11. The belt also includes at an end of the stretch material, a portion of Velcro™ hook 38 for fastening means to loops 37 for effecting belt closure about the waist.

The major axis of the slot 26 is directed substantially parallel to the direction of the upper edge 20. By having the slot formed as an oval type shape, namely without sharp corners, there is less likelihood of tearing the pouch. Moreover, the major axis of the slot is smaller than the width of the belt, thereby minimizing belt slippage in the slot. The portion of the belt which is formed by the stretch material passes through the slot so that the slot is located at about the midpoint of the stretch material. The length of the stretch material could be about eight inches.

The belt 27 is substantially parallel to the slot when it passes through the slot, and it twists about 90° as it surrounds the waist 16 of the user. By having the belt 27 include a portion of stretch loop material 35, the receptacle 11 can move relative to the body portion as a user moves position, and the waist 16 of the user moves relative to other portions of the body. The belt portion includes the portion of non-stretchable material 36 to facilitate the fit about the waist.

Adjacent to the intersection of the bottom edge 17 which is located at the joinder of each side wall portion 18 and the lip 19, there is provided means for a first securing means.

This first securing means is in the form of two strips of tape 28 measuring about 1½ inches by 4 inches. One end of each of these strips of tape 28 is attached to a respective half portion of the side wall 18 of the receptacle pouch 11 on the outside of the receptacle pouch 11. The other end of the tape is for fixation by an adhesive to a respective buttock 15 of the user. In this manner, the tape 28 is provided with a first non-adhesive surface and a second adhesive surface on the opposite end. A suitable liner can be provided to cover the adhesive surface until the tape 28 is used. The tape has no appreciable stretch characteristic.

By having the tape 28 be fixed in this substantially rigid manner relative to the buttocks 15, the bottom edge 17 and lip portion 19 of the device 10 is substantially firmly located in adjacency with the lower or rear portion of the labia majora 14. In this manner, leakage is inhibited.

On the other hand, the relative flexibility with which the top edge portion 20 of the receptacle pouch 11 can move permits for adjustment of the receptacle pouch 11 relative to the body so that a conforming shape is maintained for the receptacle in position over the labia majora 14.

A cone-shaped reservoir 29 of highly adsorbent non-woven material is located in the receptacle pouch 11. In other forms the material can be an absorbent material. The reservoir material 29 includes a wicking system 30 which passes through an orifice 23 in the intersecting edge of the receptacle pouch.

The tubing 24 is a 0.400 inch outer diameter PVC tubing having an internal diameter of about 0.300 inch. It has a very soft durometer, and is about six inches or more in length. In some cases the tubing 24 can extend up to about 30 inches with the wicking element 30 inside. The wick 30 may extend for all or part of the length of the tubing 24. The tubing 24 is sealed with the perimeter of the orifice 23 in the receptacle pouch and the tubing 24 has a removable cap at the end. The end can also be connected to a collection drain bag or bottle 31 for collecting urine.

By having the wick 30 end at a position lower than the reservoir 29, a gravity effect is achieved and urine from a void, drains from the reservoir 29 along the wick 30 into the collection drain or bag 31. The wick 30 can be located in the reservoir 29. The wick can be positioned at any convenient location within the reservoir. In another form of the device, the wick 30 is positioned substantially along the bottom edge 17 of the receptacle 11 so that a gravity effect of urine in the reservoir also works on the wick to cause urine to be absorbed by the wick 30 prior to draining into the collection bag 31. The wicking material is an absorbent or adsorbent material, but preferably an adsorbent material.

In considering the interaction of a fluid with a fibrous structure, there are two principal phenomena that need be considered: adsorption and absorption.

(1) The process of adsorption involves the collection of a fluid on the surface of a material. Some interactions can then occur, depending upon the nature of the material making up the surface, and the nature of the fluid or liquid involved. If the fluid can "wet" the surface material, it tends to spread out and wet as much of the surface as possible. If the liquid does not wet the surface, it tends to "bead up" and assume as small a surface volume as possible.

(2) The process of absorption, on the other hand, involves the penetration of the fluid into the interior of a material. This generally involves a molecular or similar attraction between the liquid and the solid material. As the solid imbibes the liquid, it tends to swell, which swelling continues until it is restricted by mechanical limits of the structure; at that point, the solid is saturated with the liquid and no further absorption takes place.

In the reservoir portion and wicking, it is preferred to form the reservoir from fibers that, of themselves, do not participate in absorption to any substantial degree. If absorbent or strongly hydrophilic fibers such as cotton or viscose rayon were employed, they would absorb the liquid involved and would swell to their maximum imbibed or swollen diameter. The swollen fibers would retain such liquid until it was removed, primarily by drying at an elevated temperature, or by gradual evaporation. There would be a modest amount of liquid contained in the void spaces between the swollen fibers, but the hydrophilic fiber surfaces would tend to attract the liquid, rather than transport it by a wicking process.

For optimum functionality, it is preferred to use hydrophobic fibers as the structural elements of the reservoir in the female urinary pouch. Such hydrophobic fibers do not imbibe the liquid and undergo swelling. Rather, with the proper rewetting character of the fiber surface, the fiber is partially wetted by the liquid. As the liquid encounters fibers that lie next to each other, it enters such capillary spaces and is moved by the attendant capillary pressure to spaces that have not yet been filled with liquid. Hence, the liquid is transported, or wicked, from regions containing liquid to regions that do not contain liquid.

By this process, the liquid can move within the structure until virtually all of the void space within the fibrous reservoir is filled. Further, as liquid is removed from one region of the fibrous reservoir, any excess liquid that is present moves into that void space through capillary pressure action. In essence, the liquid is transported from zones of high liquid content to zones of low liquid content by movement of the liquid along the surfaces of the fibers making up the reservoir.

For this action to progress effectively, the fibers employed in the reservoir structure and wicking are preferably hydrophobic, synthetic fibers. Further, such fibers must be prepared with a "finish" or surface lubricant that conveys a modest amount of wettability to the fiber, so that the wicking process can commence and continue. It is standard practice to provide fibers with a lubricating finish to facilitate the several mechanical operations that are normally applied in converting a fiber to a finished product. By addition of appropriate wetting agents to the lubricating materials, the finish can be formulated to give balanced wetting properties.

Suitable fibers for forming the liquid reservoir may include those produced from polyester, polyamide (nylon), polyolefin (such as polypropylene or polyethylene, or copolymers of propylene and ethylene) resins. The polyester fibers can be produced from homopolymer resin of polyethylene terephthalate, polybutylene terephthalate, polyethylene naphthenate, or similar polyester materials or copolymers. The nylon fibers can be produced from nylon-66 (polyhexamethylene adipate), nylon-6 (polycaprolactam) or similar polyamide or copolyamide materials. The polyolefin fibers can be produced from polypropylene, polyethylene or copolymers of propylene, ethylene, or similar olefin monomers or copolymers.

Other synthetic fibers possessing a hydrophobic nature can be used for this application; this may include, acrylic, modacrylic, cellulose acetate, vinyl fibers, spandex and other elastomeric fibers or blends of such fibers.

In order to form a reservoir and wicking that has suitable shape, integrity, and wet stability, it is necessary to incorporate binder fibers or particles in the reservoir and/or wicking. Such binder fibers or particles can be of the melting type, wherein the entire fiber or particle melts upon thermobonding of the reservoir structure and/or wicking.

A more preferred procedure is to use a bicomponent sheath/core type of binder fiber. Such a fiber has a core of higher melting point resin surrounded by a coating or sheath of lower melting point resin. For thermobonding, a temperature above the melting point of the sheath material is achieved, whereupon the sheath melts and forms a bond with any fiber touching the outer skin or sheath upon cooling. The advantage of this latter method is that the core of the binder fiber is not destroyed, but retains its fiber properties of strength and integrity throughout the thermobonding process, in contrast to the former method.

Other methods of bonding the fibrous reservoir structure can be used, but often with the introduction of some disadvantages. Such bonding may involve chemical latex binders or adhesives. Mechanical bonding, such as needle punching or high pressure waterjet entanglement can be used.

When viewed from the side in the closed position, the leading edge 32 of the reservoir 29, namely the edge 32 adjacent to the lip 19, extends past the perimeter of the lip 19. This is to a position beyond the lip 19 so that it has an abutting relationship with the lower part of the labia majora 33. This facilitates the drainage of urine from the urethra into the reservoir 29.

When located in position, a compression effect takes place on the reservoir 29 thereby pushing the reservoir 29 substantially back into the perimeter as defined by the lip 19. This is achieved when the tapes 28 are pulled tight into position on the respective buttocks 15.

The receptacle 11 has a substantially funnel-type shape forming an apex towards the drain position where the orifice 23 is located. The reservoir 29 also has a largest area adjacent to the lip 19 and a decreasing area towards the aperture location. The reservoir 29 occupies about one-half of the volume of the receptacle pouch 11.

An aspect of the invention when related to the receptacle contacting the outside of the labia majora 14 is that there is believed to be no need for a sterile collection drain, bag or bottle 31 and supporting tubing 24. This provides an important advantage since multiple different units of this invention can be used in turn with a single collection drain bag or bottle system repetitively.

Many other forms of the invention exist, each differing from others in matters of detail only.

In some situations there can be a collection device which is attached with the female anatomy within the area of the lips of the labia majora 14.

In other embodiments, for instance, instead of having an oval-shaped aperture 26 in the side wall 18 located transversely and substantially parallel to the upper edge for accommodating the stretch flexible loop, the means for fixing that loop to the receptacle pouch can be different.

Essentially, the combination of a flexible anchorage towards the top portion or edge 20 of the wall 18 of the receptacle pouch 11, and a relatively rigid engagement of the wall towards the bottom portion 17 of the receptacle pouch 11 is a desirable characteristic for effectively engaging the receptacle in a substantially leak proof manner relative to the body.

In other situations, the strips of tape 28 may adhere to the receptacle pouch 11 in different positions on the receptacle pouch.

In other situations, the reservoir 29 may occupy a different volume of the receptacle pouch 11. In further forms, the foam tape 27 may extend to a greater portion of the length of the lip namely to a position in closer adjacency to the upper edge.

Further, although the invention has been described generally in relation to a pouch, there are applications beyond a pouch type receptacle. For instance, the securing means may operate with different types of receptacles or other devices for securing to the body. The receptacles or devices can be formed of a rigid material.

Instead of a polyethylene closed-cell foam tape along the lip portion of the receptacle, other materials could be used. Materials other than vinyl could be used for the pouch.

There are aspects of the invention which are concerned with the receptacle, the reservoir and wicking material, and which are unrelated to the nature of the securing means with the body. The invention is to be determined solely by the following claims.

I claim:

1. A female urinary collection device comprising:
   a generally pouch-shaped receptacle for collecting urine from the urethral orifice of a female user, the receptacle having a bottom edge portion and a side wall portion projecting generally from the bottom edge and in a lip portion for sealing engagement with the human tissue substantially outside the area of the labia majora of the user, the side wall portion including at least two zones for anchoring securing means to the side wall, a first securing means being located at a position with the side wall substantially adjacent to the bottom edge for the pouch and for permitting the securing means to engage each of two buttocks of a user, and a second securing means being located at a position removed from the bottom edge whereby the second securing means is for securing the receptacle to a portion of the body above the external organs of generation, and the first securing device including an adhesive element, the element being for adhesive bonding with each respective buttock thereby to locate the bottom edge portion of the receptacle relatively securely in relation to the buttocks.

2. A device as claimed in claim 1 wherein the first securing device includes a pair of tapes, one tape being for connection with each respective buttock, and each tape being for adhesive bonding with a respective buttock thereby to locate the bottom edge portion of the receptacle relatively securely in relation to the buttocks.

3. The device as claimed in claim 1 wherein the second securing means includes a flexible strap, the flexible strap being for location about the waist of a user thereby to permit a degree of relative movement between the receptacle and the user in the region of the location of the second securing means.

4. The device as claimed in claim 1 including a polyethylene closed-cell foam tape located along at least a portion of the lip portion of the receptacle thereby to provide a relatively soft surface to facilitate comfort and reduce leakage between the receptacle and the body of the user.

5. The device as claimed in claim 4 wherein the foam tape extends on the lip portion for about two inches from the bottom edge towards the upper edge.

6. The device as claimed in claim 1 wherein the receptacle is formed of a vinyl material, and wherein the receptacle includes two mating side walls, each of the side walls having a lip portion, the side walls selectively spreading apart to form a pouch rim for conforming to the body shape of a user.

7. The collection device as claimed in claim 6 wherein each side wall includes an upper edge, the upper edge being separable and being located between each lip and a base, the upper edge being relatively spreadable for accommodating the shape of the user.

8. The device as claimed in claim 1 wherein the second securing means is located with the side wall portion at a position adjacent to a base, the base being at a location of the side wall portion removed from the lip portion.

9. The device as claimed in claim 8 including a reservoir of adsorbent material for location in the receptacle.

10. The device as claimed in claim 9 wherein the reservoir includes a wicking material, the receptacle includes an outlet orifice, the outlet orifice being located substantially between the base and the bottom edge, a tubing for connection to the outlet orifice for permitting removal of urine from the receptacle, and the wicking being directed from the reservoir through the orifice into the tubing.

11. The device as claimed in claim 9 wherein the reservoir is substantially cone-shaped to conform substantially to the pouch shape of receptacle, and wherein the reservoir is formed of an adsorbent, non-woven material.

12. The device as claimed in claim 9 wherein the reservoir occupies about one-half of a volume of the receptacle.

13. The device as claimed in claim 9 wherein a leading edge of the reservoir extends past the lip such that it is in abutting relationship with the labia majora.

14. The device as claimed in claim 1 including means for securing the second securing means to the side wall portion, such securing means including a substantially oval slot cut in the side wall portion for accommodating a belt of nylon stretch loop and foam material, the belt being for extending around the waist of a user.

15. The device as claimed in claim 14 wherein the oval cut includes a major axis substantially in line with an upper edge of the receptacle.

16. A female urinary collection device comprising a receptacle for collecting urine from the urethral orifice of a female user, the receptacle having a bottom edge portion and a side wall portion projecting generally from the bottom edge and in a lip portion for sealing engagement with the human tissue of the user, the side wall portion including at least two zones for anchoring securing means to the side wall, a first securing means being located at a position with the side wall and for permitting the securing means to engage each of two buttocks of a user, and a second securing means being located at a position whereby the second securing means is for securing the receptacle to a portion of the body above the external organs of generation, and the first securing device including an adhesive element, the element being for adhesive bonding with each respective buttock thereby to locate the bottom edge portion of the receptacle relatively securely in relation to the buttocks.

17. A device as claimed in claim 16 wherein the first securing device includes a pair of tapes, one tape being for connection with each respective buttock, and each tape being for adhesive bonding with a respective buttock thereby to locate the bottom edge portion of the receptacle relatively securely in relation to the buttocks.

18. A female urinary collection device comprising a receptacle for collecting urine from the urethral orifice of a female user, the receptacle having a bottom edge portion and a side wall portion projecting generally from the bottom edge and in a lip portion for sealing engagement with the human tissue of the user, the side wall portion including at least two zones for anchoring securing means to the side wall, a first securing means being located at a position with the side wall and for permitting the securing means to engage each of two buttocks of a user, and a second securing means being located at a position whereby the second securing means is for securing the receptacle to a portion of the body above the external organs of generation, and the first securing device including adhesive tape for connection with each respective buttock, thereby to locate the bottom edge portion of the receptacle relatively securely in relation to the buttocks and the second securing means including a flexible strap, the flexible strap being for location about the waist of a user thereby to permit a degree of relative movement between the receptacle and the user in the region of the location of the second securing means.

19. The device as claimed in claim 18 including a reservoir of adsorbent material for location in the receptacle.

20. The device as claimed in claim 19 wherein the reservoir includes a wicking material, the receptacle includes an outlet orifice, the outlet orifice being located substantially between the base and the bottom edge, a tubing for connection to the outlet orifice for permitting removal of urine from the receptacle, and the wicking being directed from the reservoir through the orifice and into the tubing.

* * * * *